US00PP25754P3

(12) United States Plant Patent
Schoone

(10) Patent No.: US PP25,754 P3
(45) Date of Patent: Jul. 28, 2015

(54) ***PHALAENOPSIS* ORCHID PLANT NAMED 'DIXIE DOT'**

(50) Latin Name: ***Phalaenopsis* hybrid**
Varietal Denomination: Dixie Dot

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 96 days.

(21) Appl. No.: 13/987,998

(22) Filed: Sep. 23, 2013

(65) Prior Publication Data

US 2014/0090125 P1 Mar. 27, 2014

Related U.S. Application Data

(60) Provisional application No. 61/704,989, filed on Sep. 24, 2012.

(30) Foreign Application Priority Data

Sep. 27, 2012 (NL) ..... PBR OPS957

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
CPC ..... A01H 5/02; A01H 5/00
See application file for complete search history.

*Primary Examiner* — Kent L Bell
(74) *Attorney, Agent, or Firm* — Foley & Lardner LLP; Sunit Talapatra

(57) ABSTRACT

A new and distinct *Phalaenopsis* plant named 'Dixie Dot' particularly characterized by flowers which are yellow with a red/purple marks and a red/purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Dixie Dot'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Dixie Dot'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Dixie Dot' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Dixie Dot' originated from a cross made by the inventor in 2000 in Strengweg, Heemskerk, The Netherlands. The female or seed parent is the *Phalaenopsis* cultivar designated 'Ever-Spring King', unpatented. The male or pollen parent is the *Phalaenopsis* cultivar designated '(Snow Leopard×Salu Rose)', unpatented. The new *Phalaenopsis* 'Dixie Dot' was discovered and selected by the inventor as a single flowering plant within the progeny of the stated cross in a controlled environment in 2008 in Strengweg, Heemskerk, The Netherlands.

Asexual reproduction of the new *Phalaenopsis* cultivar by tissue culture was first performed in July, 2008 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Dixie Dot', which in combination distinguish this *Phalaenopsis* as a new and distinct cultivar:

1. flowers which are yellow with red/purple marks and a red/purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Dixie Dot', the female parent 'Ever-Spring King' has yellow colored flowers with red/purple marks, the male parent '(Snow Leopard×Salu Rose)' has yellow colored flowers with red/purple spots, whereas the flowers of 'Dixie Dot' are yellow with red/purple marks (but less than the female parent).

Presently, there is no commercial cultivar to which 'Dixie Dot' can be meaningfully compared.

BRIEF DESCRIPTION OF THE PHOTOGRAPHS

The accompanying photographs illustrate the overall appearance of the new *Phalaenopsis* 'Dixie Dot' showing the colors as true as is reasonably possible with colored reproductions of this type. Colors in the photographs may differ slightly from the color values cited in the detailed botanical description, which accurately describe the color of 'Dixie Dot'.

DETAILED BOTANICAL DESCRIPTION

Figure 1:
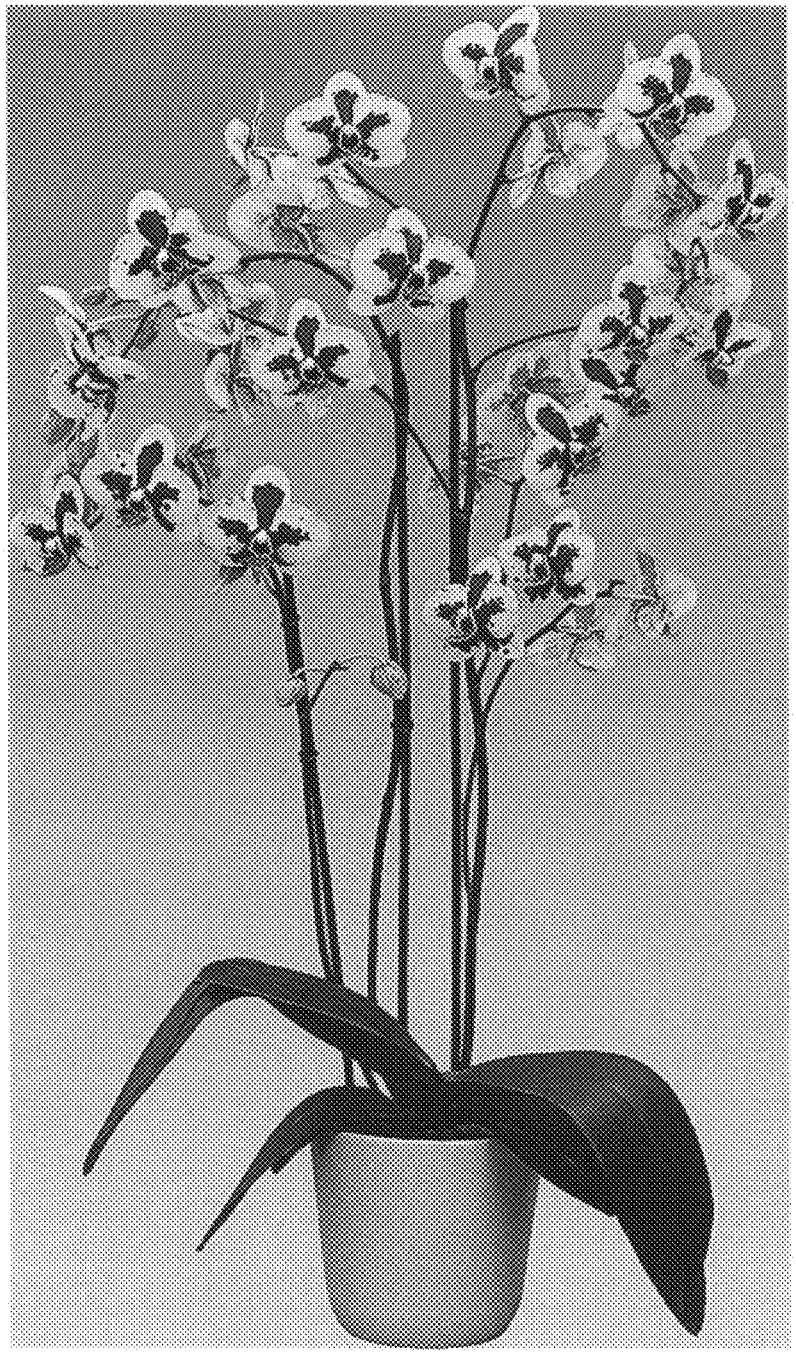
FIG. 1 shows a side view perspective of a typical flowering plant of 'Dixie Dot' in a 12 cm pot, at 16 months of age.

The new *Phalaenopsis* cultivar 'Dixie Dot' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Dixie Dot' as grown in a greenhouse in Strengweg, Heemskerk, The Netherlands, under conditions which closely approximate those generally used in commercial practice. Initially, the ideal temperature to grow plants of 'Dixie Dot' is 27° C. during the day and at night. Then, during the flowering phase of 'Dixie Dot', the ideal growing temperature is 20-22° C. during the day and 18° C. at night. Light levels for growing 'Dixie Dot' are a minimum of 5,000 lux and a maximum of 10,000 lux. A balanced fertilizer with level of 200 ppm N, 87 ppm P, 168 ppm K is applied. Duration of growth of 'Dixie Dot' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Dixie Dot' plants described is 12 months after potting.

Classification:

*Botanical.*—*Phalaenopsis* hybrid.

Parentage:

*Female or seed parent.*—*Phalaenopsis* cultivar designated 'Ever-Spring King', unpatented.

*Male or pollen parent.*—*Phalaenopsis* cultivar designated '(Snow Leopard×Salu Rose)', unpatented.

Propagation:

*Type.*—Tissue culture.

*Rooting habit and description.*—Approximately 3 mm-6 mm wide and grey/green (RHS 190B) in color; freely branching. It takes 12 weeks for plants growing in tissue culture to initiate roots.

Plant:

*Size at maturity.*—Height: about 80 cm. Spread: about 65 cm.

*Growth habit.*—Large; green (RHS 137A) leaves and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval and long, the tip is blunt and asymmetric.

*Texture.*—Smooth and leathery.

*Pubescence.*—None.

*Mature leaf length.*—About 17 to 25 cm.

*Mature leaf width.*—About 7 to 10 cm.

*Mature leaf thickness.*—About 2 mm.

*Mature leaf color.*—Upper side: RHS 137A. Under side: RHS 137C, some have a purple edge (RHS N79B).

*Leaf base.*—Acute.

*Margin.*—Entire.

*Venation.*—Pattern: parallel. Color of midvein: upper side: green (RHS 136A). Under side: green (RHS 138A).

Raceme:

*Quantity per plant.*—About 1 to 3.

*Number of flowers per raceme.*—About 5 to 20.

*Length.*—About 60 to 80 cm.

*Diameter.*—About 5 mm.

*Strength.*—Strong.

*Aspect.*—Upright.

*Texture.*—Glabrous and smooth.

*Color.*—From base grey/brown (RHS N199A) with yellow/green spots (RHS N79B).

*Internode.*—Length: about 50 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 25 mm. Diameter (at midpoint): about 18 mm. Shape: oval/egg-shaped. Color: yellow (RHS 8B) with red/purple spots (RHS 59A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
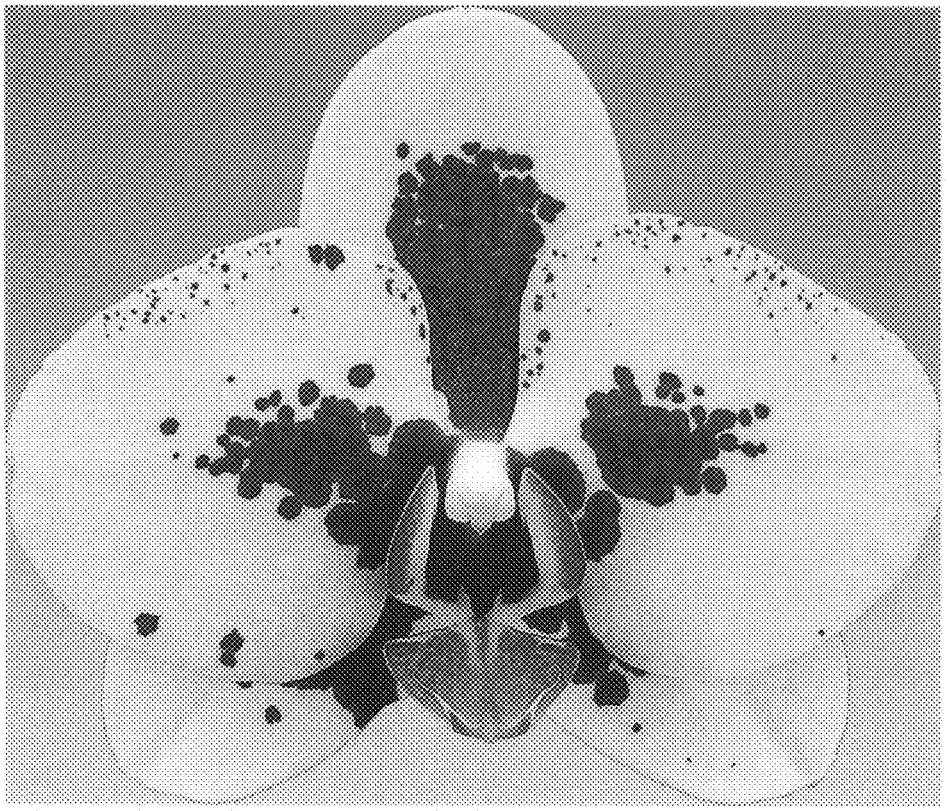
FIG. 2 shows a close-up view of a typical flower of 'Dixie Dot'.
Figure 3:
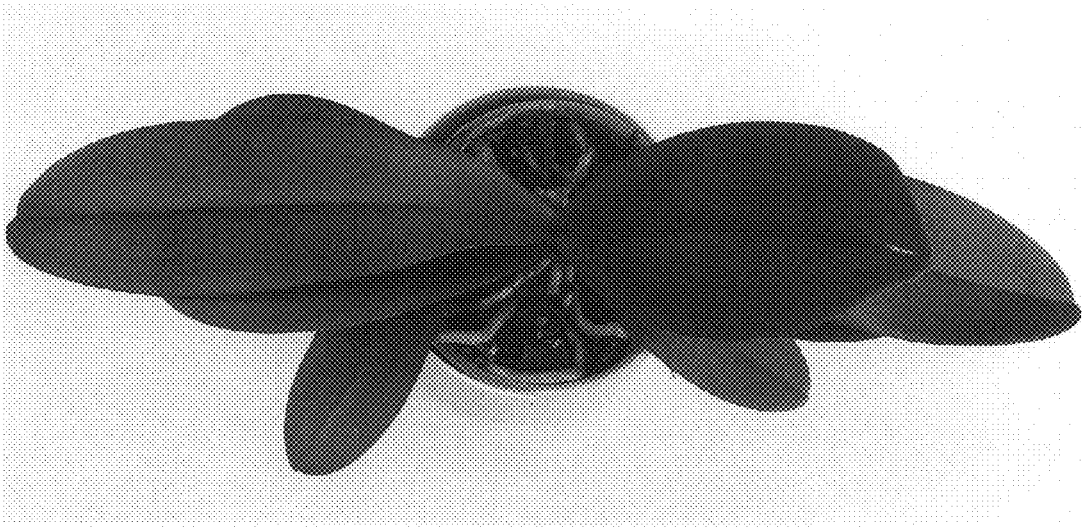
FIG. 3 shows a close-up view of the typical leaves of 'Dixie Dot'.

*Flower*.—Rate of opening: Flowers fully opened about 2 to 3 days after petal and sepal separation. Orientation at opening: slanted upward and outward. Shape: Typical shape of *Phalaenopsis* orchid, see FIG. 2. Size: Height: about 75 mm. Diameter: about 80 mm. Depth of tube: about 11 mm.

*Petals*.—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate, little triangular and weakly cupped. Apex: oval/round. Margin: entire and weakly undulate. Base: broadly ovate. Length: about 42 mm. Width: about 33 mm. Texture: Upper surface: smooth and satiny. Under surface: smooth and satiny.

*Color* (*when fully opened*).—Upper surface: Main color is yellow (RHS 10C). From the base red/purple marks and spots (RHS 59A). At the base also little bit white (RHS NN155B). Under surface: Main color is yellow (RHS 10D and RHS 10C). Some vague purple spots (RHS 59B).

*Labellum*.—Overall shape: 3-lobed with 2 prominent callosities at central junction of the lateral lobes and base of the midlobe. Lateral lobes of labellum fold upward about the column; the midlobe extends forward and is terminated by 2 short stubs appendages at the apex. Lateral lobes of the labellum are ovate in shape while the midlobe is triangular with a bump and a rib on it. Margin: entire and weakly undulate. Apex: oval. Length: about 20 mm. Width (not flattened): about 15 mm. Texture: Upper & under surface: smooth and satiny. Color (when fully opened): Midlobe, upper surface: From base yellow/orange (RHS 14A) which runs into red/purple (RHS 59A) with red/purple (RHS 72B) and on the edges some white (RHS NN155D). under surface: At the base RHS NN155B (runs in the center from top till bottom) with yellow/orange edges (RHS 14A) which runs into red/purple (RHS 59A) and then into RHS 72B. Lateral lobes, upper surface: At the base a red/purple mark (RHS 59A). The edge, from base till half way are yellow/orange (RHS14A) which runs out into red/purple edge (RHS 71A). In the center after the red/purple mark, also some white (RHS NN155C). Under surface: Base is white (RHS NN155B). Under edge little yellow/orange (RHS 14A) which runs into red/purple (RHS 71A).

*Chirri*.—Small (about 5 mm). color: first purple (RHS 72B), than yellow/orange (RHS 14B).

*Pestle* (*callosities*).—Length: about 4 mm. Width (not flattened): about 4 mm.

*Color*.—Edges and top are grey/purple (RHS 187A). Sides are yellow/orange (RHS 14C).

*Sepals*.—Arrangement: Outer whorl of petals comprises 3 sepals. Overall shape: elliptical and weakly cupped. Margin: entire and weakly undulate. Length: about 40 mm. Width: about 30 mm. Apex: Dorsal: oval/round; lateral: little pointy. Texture: Upper & under surface: smooth and satiny. Color (when fully opened): Dorsal & lateral, upper surface: at the base yellow (RHS 10C). From the base a red/purple mark (RHS 59A) with some spots around it in the same color. Under surface: Dorsal & lateral: yellow (RHS 10C) with some vague red/purple marks (RHS 59B).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 9 mm. Diameter: about 4 mm. Color: white (RHS NN155C). Some have a purple/violet haze (RHS N81D).

*Pollinia*.—Quantity: Two. Diameter: about 2.5 mm. Color: yellow/orange (RHS 15A).

*Ovary*.—Length: about 3 mm. Diameter: about 2 mm. Color: white (RHS NN155C).

*Pedicel*.—Length: about 42 mm. Diameter: about 3 mm. Texture: glabrous and smooth. Color: Close to the flower yellow/green (RHS 150D) which runs into yellow/green (RHS 144D).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Dixie Dot', as illustrated and described herein.

* * * * *